(12) United States Patent
Barak et al.

(10) Patent No.: US 7,740,651 B2
(45) Date of Patent: Jun. 22, 2010

(54) VACUUM ASSISTED TREATMENT OF THE SKIN

(75) Inventors: Menashe Barak, Haifa (IL); Shlomi Mishali, Netanya (IL); Raphi Shavit, Tel Aviv (IL); Michael Slatkine, Herzlia (IL)

(73) Assignee: Candela Corporation, Wayland, MA (US)

( * ) Notice: Subject to any disclaimer, the term of this patent is extended or adjusted under 35 U.S.C. 154(b) by 267 days.

(21) Appl. No.: 11/863,440

(22) Filed: Sep. 28, 2007

(65) Prior Publication Data

US 2009/0088823 A1    Apr. 2, 2009

(51) Int. Cl.
*A61N 5/06*    (2006.01)

(52) U.S. Cl. .......................................... 607/89; 128/898

(58) Field of Classification Search .................. 128/898; 607/88, 89
See application file for complete search history.

(56) References Cited

U.S. PATENT DOCUMENTS

| | | | |
|---|---|---|---|
| 3,982,541 A | 9/1976 | L'Esperance, Jr. | |
| 4,592,353 A | 6/1986 | Daikuzono | |
| 4,736,743 A | 4/1988 | Daikuzono | |
| 4,838,281 A | 6/1989 | Rogers et al. | |
| 4,976,709 A | 12/1990 | Sand | |
| 5,057,104 A | 10/1991 | Chess | |
| 5,059,192 A | 10/1991 | Zaias | |
| 5,066,293 A | 11/1991 | Furumoto | |
| 5,217,455 A | 6/1993 | Tan | |
| 5,226,907 A | 7/1993 | Tankovich | |
| 5,282,797 A | 2/1994 | Chess | |
| 5,312,395 A | 5/1994 | Tan et al. | |
| 5,344,418 A | 9/1994 | Ghaffari | |
| 5,401,270 A | 3/1995 | Müller et al. | |
| 5,411,502 A | 5/1995 | Zair | |
| 5,429,601 A | 7/1995 | Conley et al. | |

(Continued)

FOREIGN PATENT DOCUMENTS

DE    37 30 469    6/1988

(Continued)

OTHER PUBLICATIONS

PCT International Search Report for PCT application (PCT/IL2008/001284) (5 pages).

(Continued)

*Primary Examiner*—Henry M Johnson, III
*Assistant Examiner*—Jeffrey B Lipitz
(74) *Attorney, Agent, or Firm*—Proskauer Rose LLP

(57) ABSTRACT

An apparatus for treating skin includes a chamber defined by a surface and a rim extending from the surface. A source of vacuum is capable of removing air from inside the chamber so that air outside the chamber flows into the chamber. Impedance of the air flowing between the rim of the chamber positioned adjacent the skin surface causes the pressure inside the chamber to decrease relative to ambient. A pressure sensor can determine when the pressure inside the chamber decreases to a threshold value. A controller can receive a signal from the pressure sensor when the threshold value is reached, which causes the rate of removal of the air from inside the chamber by the source of vacuum to be increased. The rim of the chamber forms a substantially fluid tight seal with the skin. The skin is drawn toward an inner surface of the chamber.

24 Claims, 7 Drawing Sheets

U.S. PATENT DOCUMENTS

| | | | |
|---|---|---|---|
| 5,431,647 | A | 7/1995 | Purcell, Jr. et al. |
| 5,449,354 | A | 9/1995 | Konwitz et al. |
| 5,527,308 | A | 6/1996 | Anderson et al. |
| 5,530,780 | A | 6/1996 | Ohsawa |
| 5,558,660 | A | 9/1996 | Dreier |
| 5,595,568 | A | 1/1997 | Anderson et al. |
| 5,626,631 | A | 5/1997 | Eckhouse |
| 5,630,811 | A | 5/1997 | Miller |
| 5,655,547 | A | 8/1997 | Karni |
| 5,735,844 | A | 4/1998 | Anderson et al. |
| 5,745,519 | A | 4/1998 | Ruda et al. |
| 5,814,041 | A | 9/1998 | Anderson et al. |
| 5,853,407 | A | 12/1998 | Miller |
| 5,871,521 | A | 2/1999 | Kaneda et al. |
| 5,879,346 | A | 3/1999 | Waldman et al. |
| 5,885,273 | A | 3/1999 | Eckhouse et al. |
| 5,947,957 | A | 9/1999 | Morris |
| 5,961,475 | A | 10/1999 | Guitay |
| 5,964,749 | A | 10/1999 | Eckhouse et al. |
| 6,011,890 | A | 1/2000 | Neuberger |
| 6,096,029 | A | 8/2000 | O'Donnell, Jr. |
| 6,120,497 | A | 9/2000 | Anderson et al. |
| 6,132,392 | A | 10/2000 | Stone |
| 6,142,650 | A | 11/2000 | Brown et al. |
| 6,149,645 | A | 11/2000 | Tobinick |
| 6,165,170 | A | 12/2000 | Wynne et al. |
| 6,185,356 | B1 | 2/2001 | Parker et al. |
| 6,197,020 | B1 | 3/2001 | O'Donnell, Jr. |
| 6,214,034 | B1 | 4/2001 | Azar |
| 6,261,310 | B1 | 7/2001 | Neuberger et al. |
| 6,264,649 | B1 | 7/2001 | Whitcroft et al. |
| 6,273,884 | B1 | 8/2001 | Altshuler et al. |
| 6,280,438 | B1 | 8/2001 | Eckhouse et al. |
| 6,508,813 | B1 | 1/2003 | Altshuler |
| 6,530,920 | B1 | 3/2003 | Whitcroft et al. |
| 6,544,259 | B1 | 4/2003 | Tsaliovich |
| 6,562,050 | B1 * | 5/2003 | Owen .................... 606/131 |
| 6,662,054 | B2 | 12/2003 | Kreindel et al. |
| 7,108,689 | B2 | 9/2006 | Eckhouse et al. |
| 7,184,614 | B2 | 2/2007 | Slatkine |
| 2002/0012860 | A1 | 1/2002 | Yoo |
| 2002/0013602 | A1 | 1/2002 | Huttner |
| 2002/0034012 | A1 | 3/2002 | Santoro et al. |
| 2002/0128600 | A1 | 9/2002 | Nissels |
| 2002/0128635 | A1 | 9/2002 | Altshuler et al. |
| 2002/0169442 | A1 | 11/2002 | Neev |
| 2003/0083536 | A1 | 5/2003 | Eshel et al. |
| 2004/0077977 | A1 | 4/2004 | Ella et al. |
| 2004/0082940 | A1 | 4/2004 | Black et al. |
| 2004/0254599 | A1 | 12/2004 | Lipoma et al. |
| 2005/0147137 | A1 | 7/2005 | Slatkine |
| 2005/0215987 | A1 | 9/2005 | Slatkine |
| 2005/0234527 | A1 | 10/2005 | Slatkine |
| 2005/0251117 | A1 * | 11/2005 | Anderson et al. ............... 606/9 |
| 2005/0251118 | A1 * | 11/2005 | Anderson et al. ............... 606/9 |
| 2005/0261584 | A1 | 11/2005 | Eshel et al. |
| 2006/0013533 | A1 | 1/2006 | Slatkine |
| 2006/0189964 | A1 * | 8/2006 | Anderson et al. ............... 606/9 |
| 2006/0211958 | A1 | 9/2006 | Rosenberg et al. |
| 2006/0241573 | A1 * | 10/2006 | Roersma et al. ................ 606/9 |
| 2006/0259102 | A1 | 11/2006 | Slatkine |
| 2006/0293722 | A1 * | 12/2006 | Slatkine et al. ............... 607/46 |
| 2007/0027411 | A1 * | 2/2007 | Ella et al. ....................... 601/7 |
| 2007/0032763 | A1 | 2/2007 | Vogel |
| 2007/0179482 | A1 | 8/2007 | Anderson |
| 2007/0219532 | A1 * | 9/2007 | Karpowicz et al. .......... 604/540 |
| 2007/0230520 | A1 | 10/2007 | Mordaunt et al. |
| 2007/0255355 | A1 * | 11/2007 | Altshuler et al. .............. 607/86 |
| 2008/0119830 | A1 | 5/2008 | Kamstad et al. |
| 2008/0123342 | A1 | 5/2008 | Gluszczak et al. |
| 2008/0215039 | A1 | 9/2008 | Slatkine |

FOREIGN PATENT DOCUMENTS

| | | |
|---|---|---|
| DE | 198 49 301 | 4/2000 |
| EP | 0 103 664 | 3/1984 |
| EP | 0 761 257 | 3/1997 |
| EP | 0 880 940 | 12/1998 |
| EP | 0 933 096 | 8/1999 |
| EP | 1 031 324 | 8/2000 |
| EP | 1 116 476 | 7/2001 |
| EP | 1 168 535 | 1/2002 |
| GB | 1 494 324 | 12/1977 |
| JP | 2001-212231 | 8/2001 |
| JP | 2005-87520 | 4/2005 |
| WO | 99/27863 | 6/1999 |
| WO | 99/46005 | 9/1999 |
| WO | 00/60711 | 10/2000 |
| WO | 00/72771 | 12/2000 |
| WO | 01/37922 | 5/2001 |
| WO | 03/049633 | 6/2003 |
| WO | 03/103523 | 12/2003 |
| WO | 2004/004803 | 1/2004 |
| WO | 2005/009266 | 2/2005 |
| WO | 2005/112815 | 12/2005 |
| WO | 2006/052745 | 5/2006 |
| WO | 2007/015247 | 2/2007 |

OTHER PUBLICATIONS

Effects of Tissue Optical Clearing, . . . Lasers Light with Tissue (Vergas et al.) in Laser in Surgery and Medicine, Sep. 13, 2001, p. 26.

\* cited by examiner

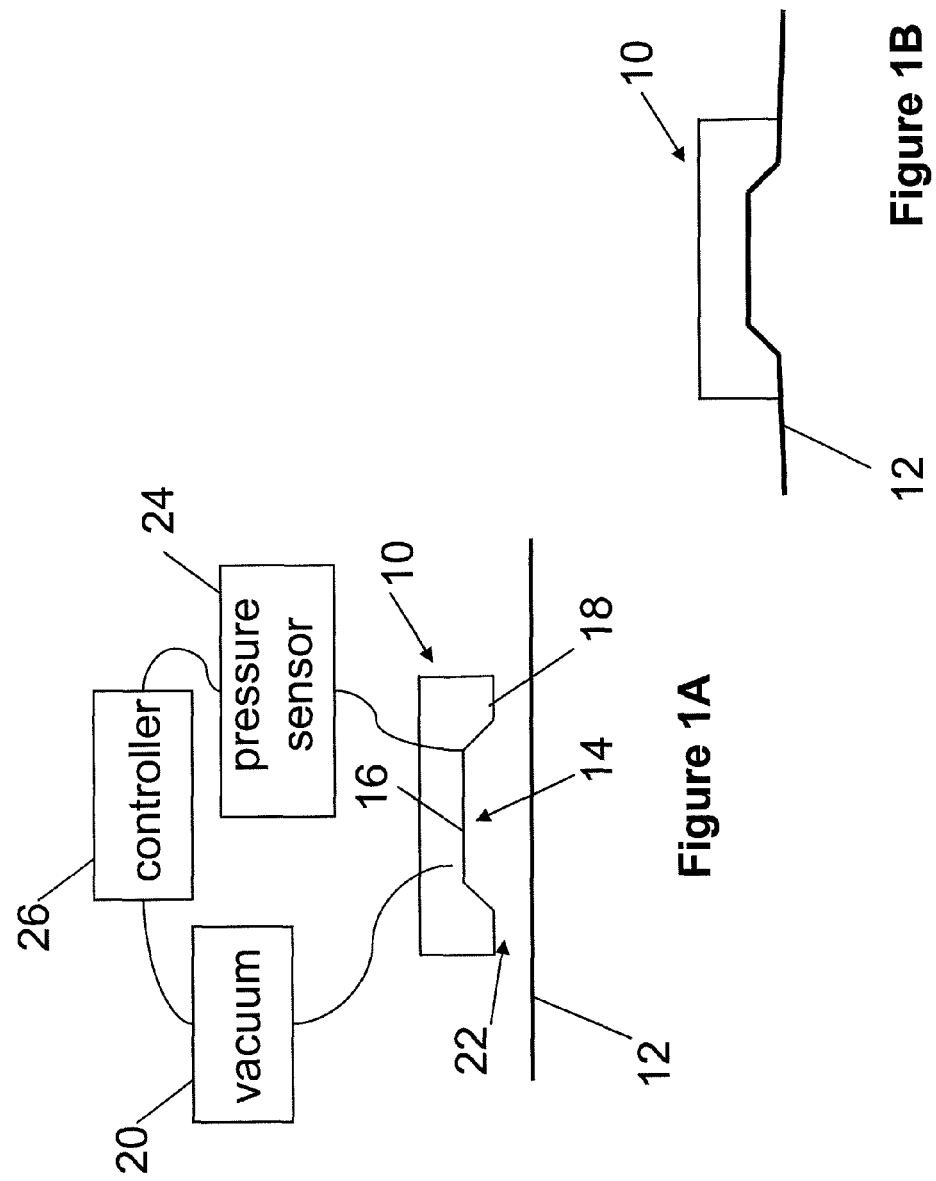

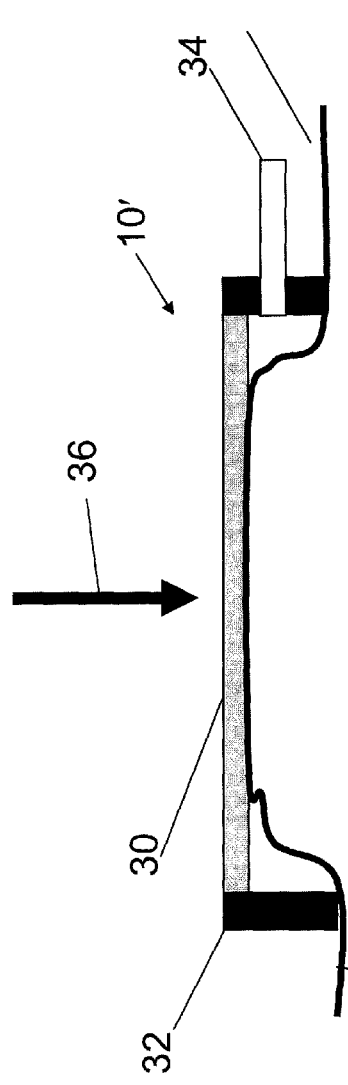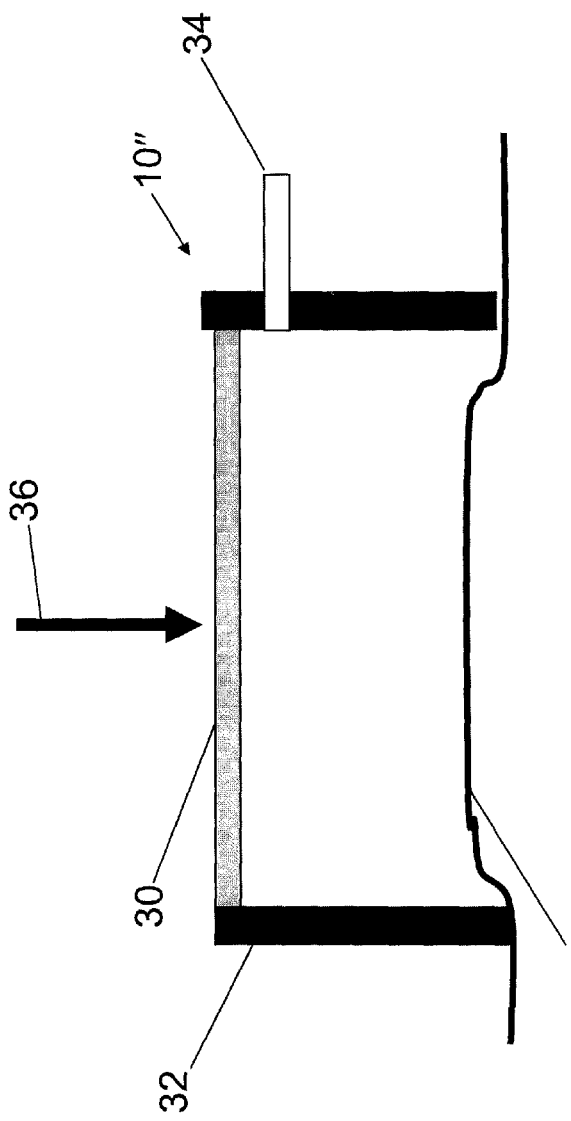

VACUUM ASSISTED TREATMENT OF THE SKIN

FIELD OF THE INVENTION

The invention is related to vacuum assisted treatments of the skin, and more particularly to creating a partial vacuum over the skin using a chamber positioned adjacent a surface of the skin in a target region.

BACKGROUND OF THE INVENTION

Vacuum assisted treatment of the skin has recently been described in several patent applications, including: U.S. patent application Ser. No. 11/498,456; U.S. patent application Ser. No. 11/401,674; EP Patent Application No. 050007952.4; U.S. patent application Ser. No. 11/057,542; U.S. patent application Ser. No. 10/498,382; and PCT/IL02/00635, the disclosures of which are herein incorporated by reference in their entirety. Clinical applications of vacuum assisted treatments of the skin include, among others, light based aesthetic treatments of the skin such as hair removal, treatment of pigmented lesions, and treatment of vascular lesions as well as medical treatments such as painless injections. An evacuation chamber, which is currently utilized for pain reduction as well as to increase efficacy and safety of light based aesthetic treatments, can use a micro-switch to enable the generation of vacuum in the evacuation chamber. When the operator places the chamber contacts the skin on the treatment site, the switch is depressed and the air is removed from the vacuum chamber. This can be achieved by slightly pressing the skin while placing the evacuation chamber over the treatment site, resulting in the activation of the micro-switch and the activation of the vacuum.

Although generally satisfactory, a disadvantage of the utilization of a micro-switch on the skin can result if the skin lacks stiffness or rigidity. While pressing the skin for the activation of the micro-switch, the skin can recede. The receding degree depends on the specific patient. Skin receding is particularly significant in obese patients or in soft areas such as the axilla or bikini line or the chin. As a result, the micro-switch may not be activated, and evacuation over the skin may not occur. Consequently, a treatment may be more difficult, or in certain circumstances, may not be feasible.

SUMMARY OF THE INVENTION

The invention features, in one embodiment, a vacuum assisted treatment device including a chamber that can be used to partially evacuate air over a target region of skin. The device need not push upon or against flexible skin when placed on or near the skin. Instead, the device senses when the chamber is adjacent or proximate the skin, and can begin to generate vacuum. Furthermore, the device can include a mechanism to deactivate the vacuum so that the device can be easily and rapidly moved between target regions.

In one aspect, the invention features a method of treating skin. The method includes removing air from inside a chamber positioned adjacent a surface of the skin in a target region. The air outside the chamber flows into the chamber. Impedance of the air flowing between a rim of the chamber and the skin surface causes the pressure inside the chamber to decrease relative to ambient. The pressure inside the chamber decreases to a threshold value. The rate of removal of the air from inside the chamber is increased upon sensing the threshold value. The rim of the chamber forms a substantially fluid tight seal with the skin surrounding the target region. The skin of the target region is drawn toward an inner surface of the chamber.

In another aspect, the invention features an apparatus for treating skin. The apparatus includes a chamber defined by a surface and a rim extending from the surface. A source of vacuum is in fluid communication with the chamber. The source of vacuum is capable of removing air from inside the chamber so that air outside the chamber flows into the chamber. Impedance of the air flowing between the rim of the chamber positioned adjacent the skin surface causes the pressure inside the chamber to decrease relative to ambient. A pressure sensor is in fluid communication with the chamber. The pressure sensor determines when the pressure inside the chamber decreases to a threshold value. A controller is in electrical communication with the source of vacuum and the pressure sensor. The controller receives a signal from the pressure sensor when the threshold value is reached, which causes the rate of removal of the air from inside the chamber by the source of vacuum to be increased. The rim of the chamber forms a substantially fluid tight seal with the skin. The skin is drawn toward an inner surface of the chamber.

In yet another aspect, the invention features an apparatus for treating skin. The apparatus includes means for removing air from inside a chamber positioned adjacent a surface of the skin in a target region. The air outside the chamber flows into the chamber. Impedance of the air flowing between a rim of the chamber and the skin surface causes the pressure inside the chamber to decrease relative to ambient. The apparatus includes means for sensing pressure inside the chamber decreasing to a threshold value. The apparatus includes means for increasing the rate of removal of the air from inside the chamber upon sensing the threshold value. The rim of the chamber forms a substantially fluid tight seal with the skin surrounding the target region. The skin of the target region is drawn toward an inner surface of the chamber.

In other examples, any of the aspects above, or any apparatus or method described herein, can include one or more of the following features.

In various embodiments, electromagnetic radiation is delivered to treat the skin of the target region. An energy source can provide treatment radiation. The energy source can be in electrical communication with the controller, which triggers the energy source to deliver treatment radiation upon decreasing the pressure inside the chamber to a second threshold value. The surface of the chamber can include a transparent window, and the treatment radiation is delivered through the transparent window to the target region of skin. In some embodiments, the surface of the chamber includes a translucent window that causes at least a portion of the treatment radiation to be diffused as the treatment radiation is delivered to the target region of skin.

In some embodiments, the skin is drawn into contact with the inner surface of the chamber. A pressure sensor in fluid communication with the chamber can be used to sense the pressure inside the chamber. The chamber can be positioned one or more of near, adjacent, or proximate the surface of the skin. In certain embodiments, the chamber can be positioned about 0.01 mm to about 3 mm from the surface of the skin before the rate of removal of air is increased. In certain embodiments, the chamber can be positioned in contact with the surface of the air before the rate of removal of air is increased without creating a substantially fluid tight seal.

In various embodiments, the rate of removal of the air from inside the chamber can be modulated by repeatedly turning on and off a source of vacuum in fluid communication with the chamber. The rate of removal of the air from inside the chamber can be increased using a second source of vacuum. The second source of vacuum can be in fluid communication with the chamber and electrical communication with a controller, which can activate the second source of vacuum when the threshold value is reached.

The chamber can be capable of forming the substantially fluid tight seal between the rim of the chamber and soft skin. The substantially fluid tight seal can be released by decreasing the rate of removal of the air from inside the chamber after a predetermined time interval following achieving the threshold value. The rate of removal of air can be decreased using a mechanism that introduces air into the chamber. In some embodiments, the substantially fluid tight seal can be released by introducing air into the chamber after a predetermined time interval following achieving the threshold value. The apparatus can include a distance gauge to facilitate placement of the chamber at, adjacent, near, or proximate to the skin. In certain embodiments, an index matching layer can be disposed on an outer surface of the chamber to facilitate delivery of the electromagnetic radiation.

In certain embodiments, a lubricant can be disposed on a surface of the skin, and the lubricant can be used to facilitate movement of the chamber to a second target region of the skin. In some embodiments, an index matching layer is disposed on a surface of the skin to facilitate delivery of the electromagnetic radiation treating the skin.

In various embodiments, a treatment can be provided for one or more of hair removal, pigmented lesions, tattoo removal, lipid rich tissue, vascular lesions, acne, skin tightening, skin remodeling, and skin rejuvenation. In certain embodiments, an injection can be delivered through a surface of the chamber into the skin to provide a vaccine, collagen, insulin, or botox. An injector (e.g., a needle or syringe) can be used.

Other aspects and advantages of the invention will become apparent from the following drawings and description, all of which illustrate the principles of the invention, by way of example only.

BRIEF DESCRIPTION OF THE DRAWINGS

The foregoing and other objects, feature and advantages of the invention, as well as the invention itself, will be more fully understood from the following illustrative description, when read together with the accompanying drawings which are not necessarily to scale.

FIGS. 1A and 1B show an apparatus, including a chamber, for treating skin.

FIGS. 2A and 2B show additional exemplary embodiments of apparatus for treating skin.

DESCRIPTION OF THE INVENTION

Figure 3:
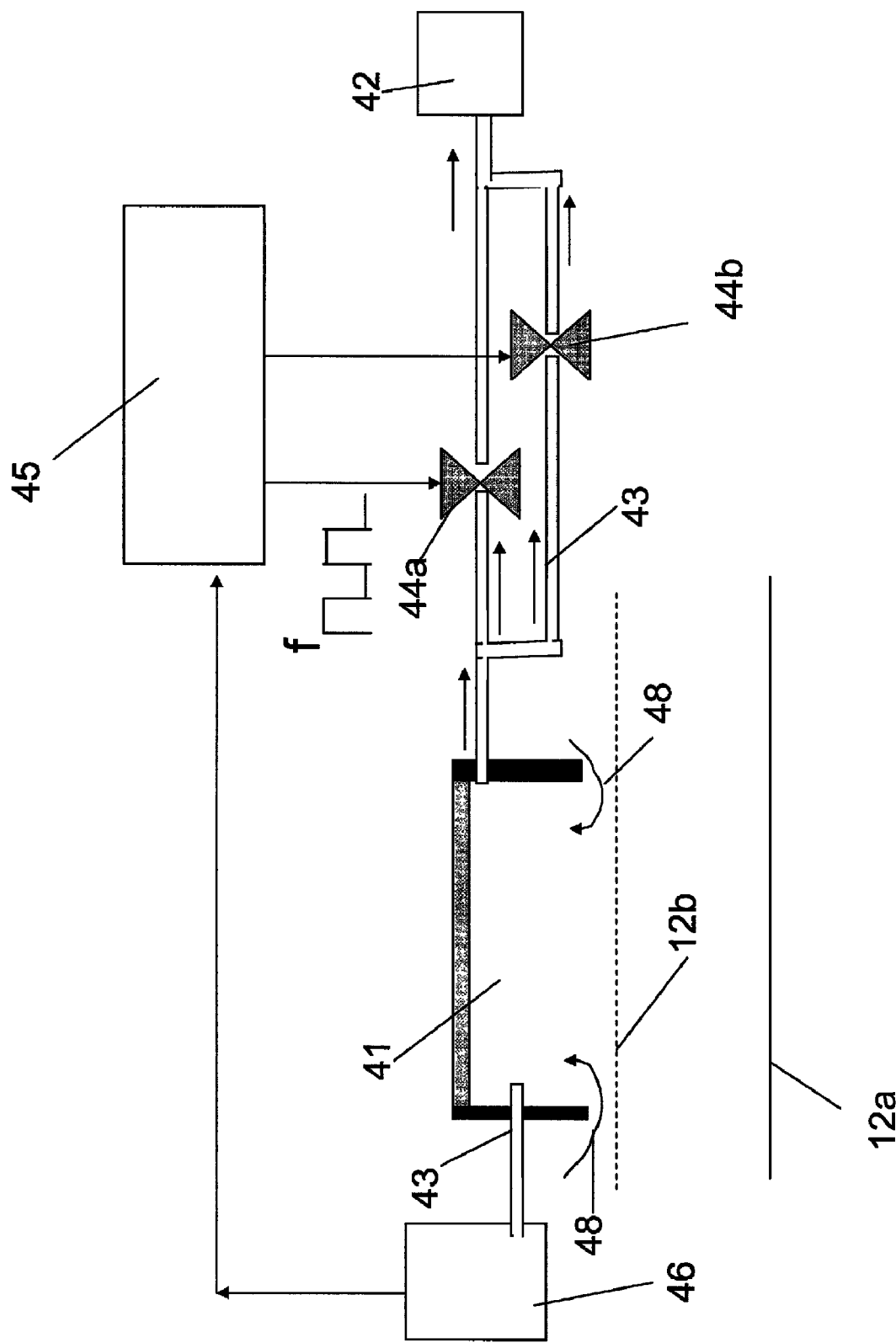
FIG. 3 shows a block diagram of a system for treating skin.

FIG. 1A shows an apparatus 10 for treating skin 12. The apparatus 10 includes a chamber 14 defined by a surface 16 and a rim 18 extending from the surface. A source 20 of vacuum is in fluid communication with the chamber 14. The source 20 of vacuum is capable of removing air from inside the chamber 14 so that air outside the chamber 14 flows into the chamber 14. Impedance of the air flowing between 22 the rim 18 of the chamber positioned adjacent the skin 12 surface causes the pressure inside the chamber 14 to decrease relative to ambient. A pressure sensor 24 is in fluid communication with the chamber. The pressure sensor 24 determines when the pressure inside the chamber 14 decreases to a threshold value. A controller 26 is in electrical communication with the source 20 of vacuum and the pressure sensor 24. The controller 26 receives a signal from the pressure sensor 24 when the threshold value is reached, which causes the rate of removal of the air from inside the chamber 14 by the source 20 of vacuum to be increased. FIG. 1B shows the skin 12 is drawn toward an inner surface of the chamber 14. The rim 18 of the chamber forms a substantially fluid tight seal with the skin 12.

The apparatus 10 can provide vacuum to partially evacuate the chamber 14 positioned at or near the skin. The apparatus 10 can be used in light based aesthetic treatments as well as in other skin treatments including injections, ultrasound treatments, and other vacuum assisted treatments. An injector is described in U.S. patent application Ser. No. 11/498,456, herein incorporated by reference in its entirety. An injection can include one or more of vaccines, mesotherapy, collagen injections, insulin injections, botox injections, intramuscular injections, and dermal injections.

The chamber 14 can compress and flatten the treated elevated skin as a result of partially evacuating the chamber. FIG. 2A shows an apparatus 10' including a window 30 as the surface and side walls 32 forming the rim. The window 30 can be a transparent window, or a substantially transparent window, e.g., a translucent window. A conduit 34 connects the chamber to a source of vacuum. Skin compression resulting from drawing the skin against the surface or window of the chamber can result in pain reduction by gate theory. FIG. 2B shows an embodiment of an apparatus 10" where the side walls 32 of the chamber are longer and the surface of the window 30 does not contact the skin surface 12 during evacuation. In FIGS. 2A and 2B, a treatment beam can be delivered through the window 30 to treat the skin. A translucent window can cause the radiation to be diffused or scattered as the radiation is delivered to the skin.

In certain embodiments, a lubricant can be disposed on a surface of the skin, and the lubricant can be used to facilitate movement of the chamber to a second target region of the skin. A sapphire translucent window can preserve its translucent properties even if residual lubricant is present on its diffusing surface, which may be in contact with the skin. This is advantageous since a diffusing window is eye safe. Before firing a treatment pulse, the lubricant, or at least a portion thereof, can be removed from the surface of the skin by the vacuum.

FIG. 3 shows a block diagram of a system for treating skin. An evacuation chamber 41 is connected to a vacuum pump assembly 42 through via a conduit 43 and solenoids valve 44. The vacuum pump can be model 70060213 available from Thomas (USA). A programmable electronic controller 45 can control the opening or closing of the valves 44. The controller can be a model RCM 3600 available from RABIT (USA). The chamber 41 is also fluidly connected to a pressure sensor 46 (e.g., model VUS 11-AR available from PISCO). The controller 45 can periodically open and close the valve 44a at a repetition rate while valve 44b is closed. Valve 44a can be a fast valve (e.g., model HKSL available from Humphrey). The periodic opening and closing of valve 44a can be performed at a rate of f=2-5 Hz, although other rates such as 0.01-1000 Hz can be used. As a result, the average pressure P inside the evacuation chamber 41 is slightly lower than about 1 atmosphere when the evacuation chamber is far from the treatment skin 12a. While bringing the evacuation chamber close to the surface of the skin 12b, air flow 48 from the surrounding air to the chamber space which is slightly evacuated (due to the periodic opening and closing of the vacuum valve system), is impeded. A typical impeding distance between the evacuation chamber opening and the skin (position 12b) is about 0.01 mm to about 3 mm, although larger and smaller distance can result. As a result of impeded flow, the pressure inside the chamber can decrease as the chamber is partially evacuated. The pressure drop is detected by the pressure sensor 46. Once pressure reading of the pressure sensor gets lower than a preset threshold limit, Pth, the controller 45 can open valve 44b, which enables a strong and fast evacuation of air from the evacuation chamber. In some embodiments, a pressure drop of 50 millibars in the chamber within 30 ms during periodic activation of valve 44a can be achieved. The threshold pressure for activation of valve 44b can be set at, for example, Pth=50 millibars below 1 atmosphere.

Once valve 44b is open, the vacuum level achieved in the chamber 41 can reach 50 millibars-1000 millibars, depending on a preset value and the opening level of valve 44b. Normally, the vacuum level is preset to 600-700 millibars. Pain inhibition by gate theory, as described in U.S. patent application Ser. No. 11/498,456, for example, is attained at 400-1000 millibars of pressure below ambient. Once valve 44b is opened and vacuum is set in chamber 41, the skin is drawn toward the chamber and elevated. Drawing the skin toward the surface of the chamber can be referred to as automatic generation of vacuum because a microswitch or other initiator is not used to generate the vacuum when the chamber is placed proximate to the skin surface.

The skin can be spaced from the surface or window of the chamber, or the skin can contact the surface or window of the chamber. A substantially fluid tight seal can be achieved between the rim of the chamber and the skin surface. In some embodiments, a substantially fluid tight seal is achieved between the surface of the target region of skin and/or the chambers walls. The seal can be improved by applying to the skin a lubricating fluid such as gel, oil or water. The lubricating fluid can include a detergent.

Figure 4:
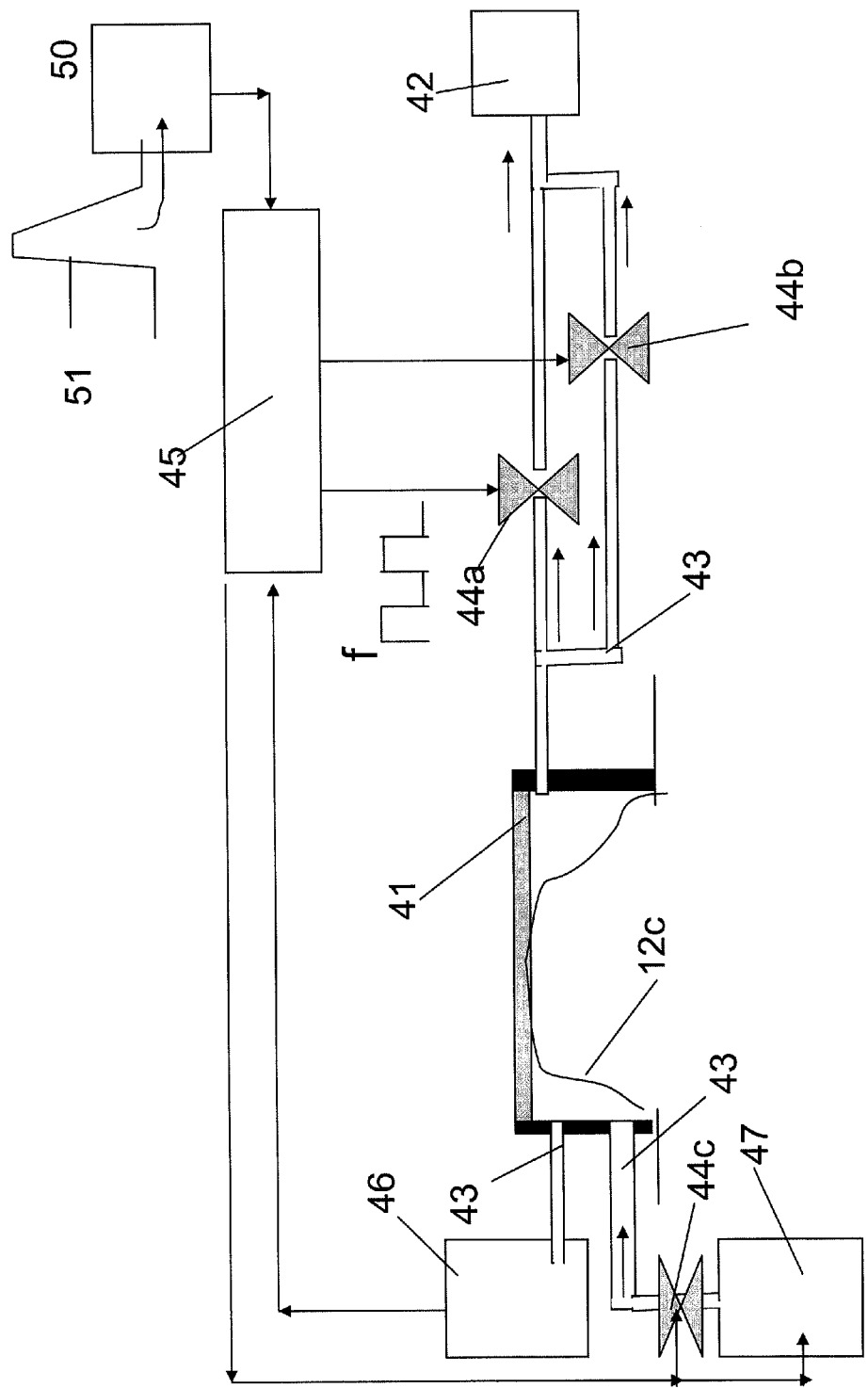
FIG. 4 shows another block diagram of a system for treating skin.

FIG. 4 shows another block diagram of a system for treating skin. The evacuation chamber 41 can be connected to a second pump 47 which pumps air into the chamber 41 and releases the vacuum through a valve 48 which is activated by the controller 45. The air can be pumped into the chamber once a treatment light pulse has been applied to the skin. A light detection assembly 50, which can include a silicon photodiode, an amplifier, and a high pass filter can detect the fall of the treatment light pulse 51, which is scattered in the treatment room and feeds the controller 45 with a signal at the pulse termination time. A treatment pulse can fall after about 1 ms. The controller can open a valve 48 and activate pump 47. The vacuum release by a fast active pump can be used to ensure rapid application of a treatment pulse to the next treatment site.

An evacuation chamber can be operated at a rapid rate of about 0.6 sec between treatment pulses while gliding on skin (e.g., obese skin) without the skin receding. Skin receding can be prevented because the chamber need not be pressed into the skin to initiate the vacuum.

Figure 5:
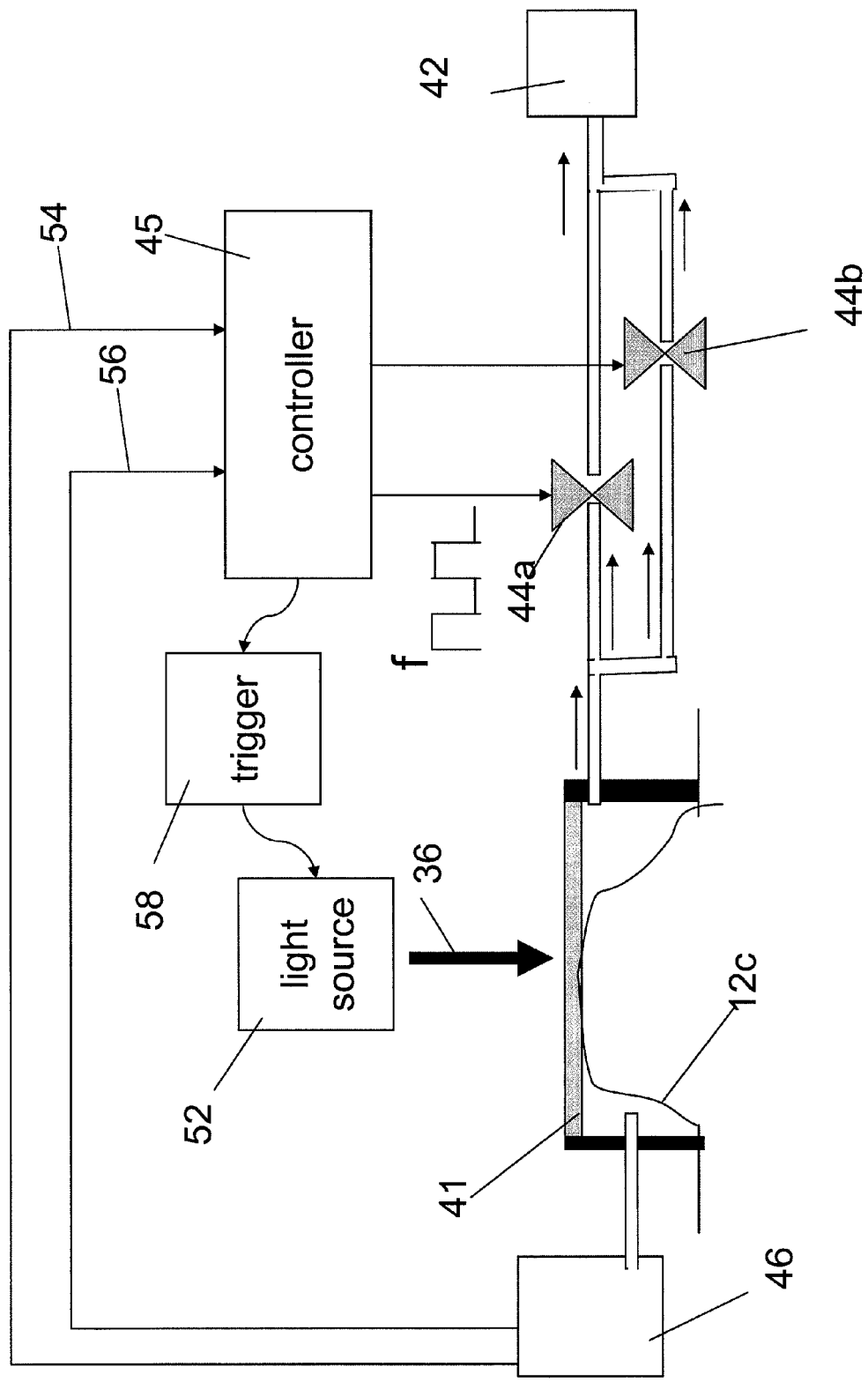
FIG. 5 shows another block diagram of a system for treating skin.

FIG. 5 shows another block diagram of a system for treating skin. The system includes electronic circuitry to drive a light source 52. The circuitry can be part of the controller 45, which can be in electrical communication with the treatment light source 52. In certain embodiments, the treatment light source 52 can be a coherent or incoherent source of light. The treatment light source 52 can be a laser, a lamp, an intense pulsed light (IPL) system, a fluorescent pulsed light (FPL) system, a radio frequency generator, an ultrasound source, or a combination of these. The lower average pressure in the evacuation chamber 41 due to vacuum modulation with valve 44a is sensed by pressure sensor 46 and triggers the creation of deeper vacuum by valve 44b. Pressure sensor 46 delivers a first pressure signal 54 that causes the controller 45 to trigger the deeper vacuum. After the rate of flow is increased and the deeper vacuum is generated, the pressure sensor unit 46 delivers a second pressure signal 56 to the controller 45 with a short preset delay. A preset delay can be about 0.1-0.7 sec, e.g., 0.1-0.2 sec. The controller 45 sends a signal to the triggering unit 58 for the light source 52. The trigger signal can include the preset delay, which can be determined by the skin elevation time (typically 0.1-0.2 sec) and possible jitter in the light source triggering unit. The triggering unit 58 triggers the light source 52 to deliver the treatment radiation 36 to administer a skin treatment.

In certain embodiments, the light source 52 can be attached to the evacuation chamber 41. For example, the evacuation chamber 41 can be attached to the distal end of a handpiece used to deliver light from the light source 52. For example, the evacuation chamber 41 can be integrated into the handpiece. In other embodiments, the light source 52 and the evacuation chamber 41 are removable from one another. For example, the evacuation chamber 41 can be attachable to a handpiece used to deliver light from the light source 52. For example, the evacuation chamber 41 can be an attachment for the handpiece.

Figure 6:
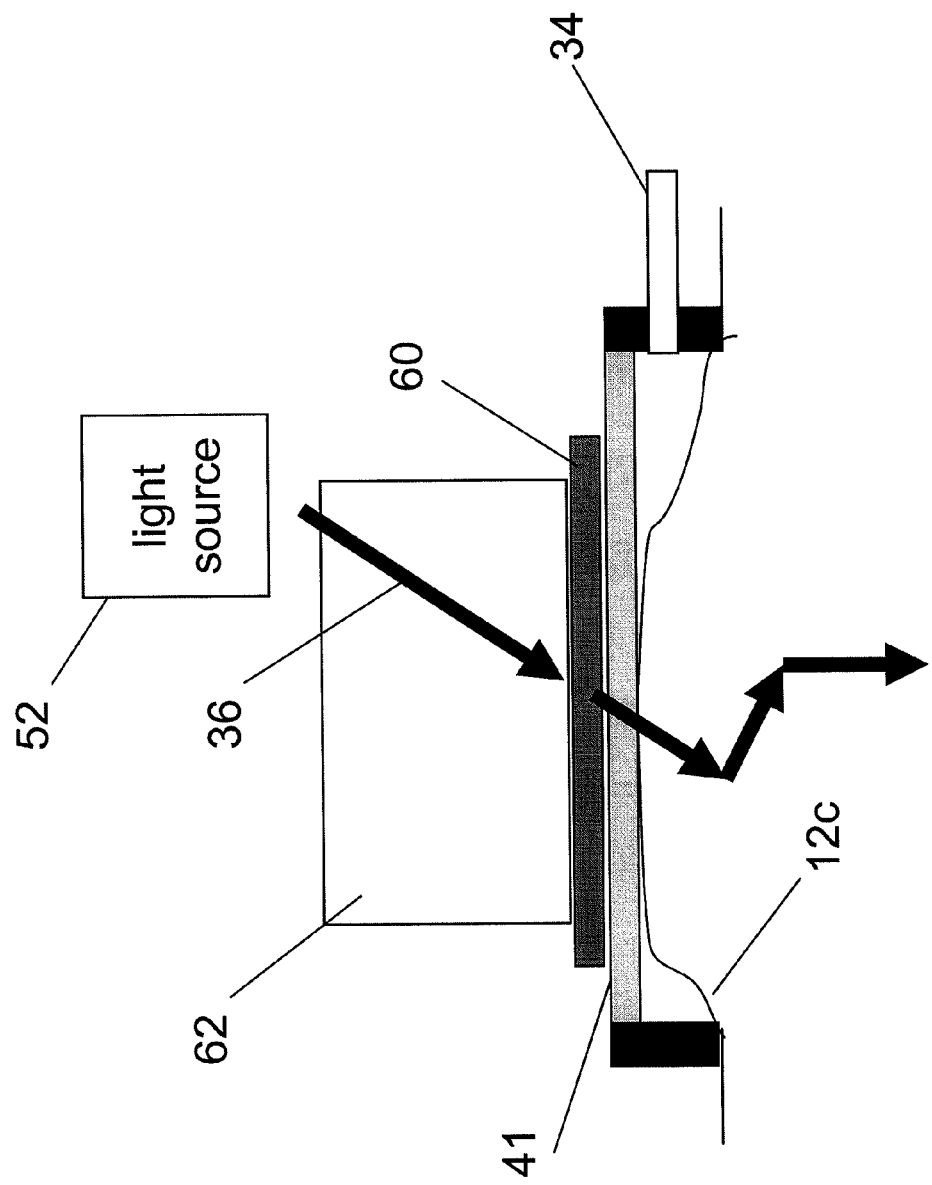
FIG. 6 shows an embodiment of a system for treating skin.

FIG. 6 shows a light source 52 used in conjunction with an evacuation chamber 41. Light is delivered using a window (transparent or translucent) of the evacuation chamber 41. Since air can be present between the light source 52 and the window of the evacuation chamber 41, refractive index mismatch can generate energy losses (e.g., reflection of light backward to the light guide or scattering). An index matching layer 60 can be disposed on the surface of the window of the evacuation chamber 41. The index matching layer 60 can be a liquid, a gel, and/or a thin transparent polymer layer (e.g., a silicone layer available from Roberts (USA)). The polymer layer can be about 0.8 mm thick. A waveguide 62 can also facilitate delivery of the light from the light source 52 to the skin. Using an index matching layer 60 can enhance efficacy of a treatment by about 20%. The polymer layer can be a polyurethane layer, silicone layer or other soft material, which is preferably transparent, but also may be translucent, to the treatment light. The polymer layer can be a soft polymer and/or a soft polymer strip with an adhesive.

Figure 7:
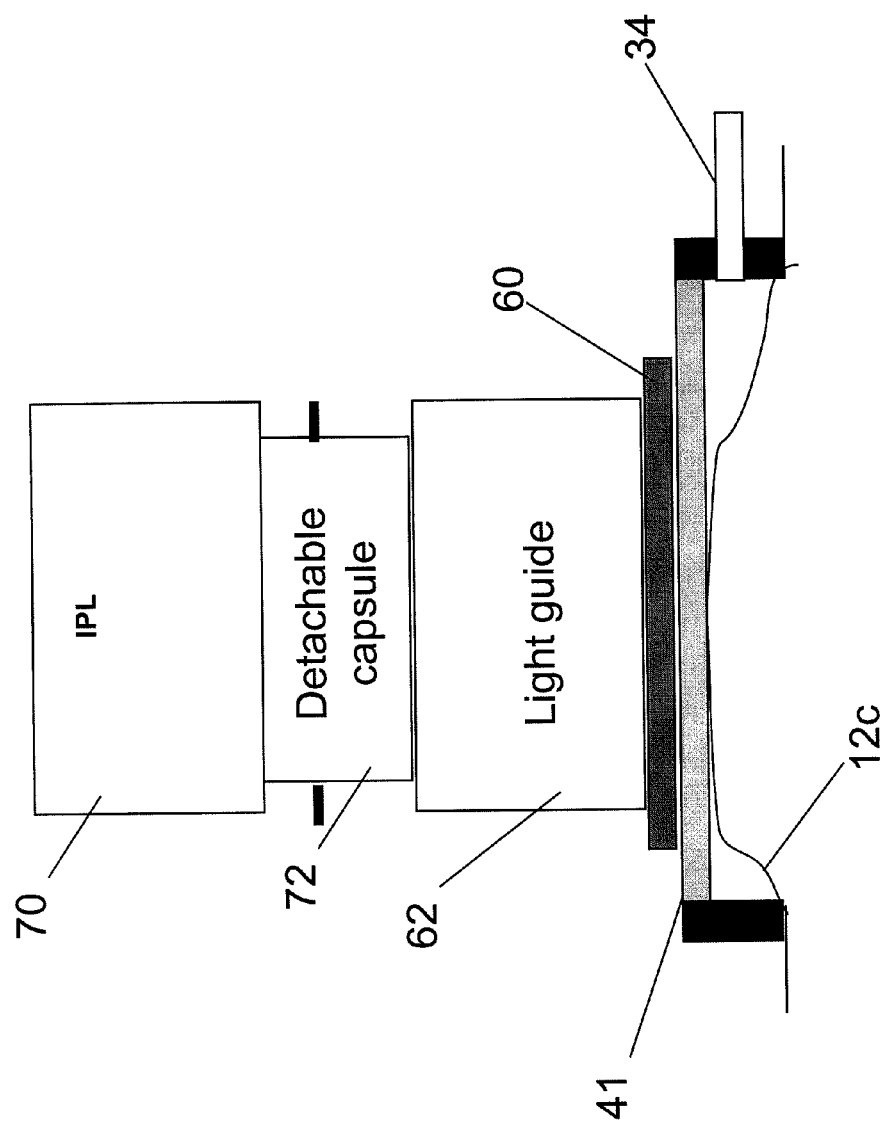
FIG. 7 shows an embodiment of a system for treating skin.

FIG. 7 shows an embodiment of an IPL light source 70 used in conjunction with the evacuation chamber 41. The IPL light source 70 includes a capsules 72, which can be a filter to filter light to optimize the light for different treatment applications. The capsule 72 can be detachable, and can include a fluorescent filter. The capsule 72 can be cylindrical or rectangular shaped. The capsule 72 can be chilled, e.g., by a flowing liquid, a thermoelectric cooler, or air. The IPL light source 70 and the capsule 72 can be include a flashlamp, e.g., a Xenon flashlamp produced by Herraus (Germany), an optical reflector, e.g., a Lambertian ceramic material or a coated metallic material, a coolant, a window to couple the flashlamp light toward the skin, a light guide, electrical connections to the high voltage source which activate the flashlamp, and appropriate inlets and outlets for water cooling.

In various embodiments, the size of the window of evacuation chamber is about 10 mm and 100 mm, although larger or smaller windows can be used depending on the application.

In various embodiments, the level of vacuum during a treatment is about 100-1000 millibars, although larger or smaller values can be used depending on the application.

In various embodiments, the level of vacuum for initiation of high vacuum level is about 10-100 millibars, although larger or smaller values can be used depending on the application.

In various embodiments, the vacuum can be modulated from no modulation (0 Hz) to about 1000 Hz, although larger or smaller values can be used depending on the application. Vacuum modulation can result from repetitively turning on and off a vacuum valve (e.g., valve 44a or 44b).

In various embodiments, the height of the chamber is about 1-40 mm, although larger or smaller values can be used depending on the application. The lateral size (parallel to the skin) of the chamber can be larger than 10 mm.

In various embodiments, the chamber is positioned adjacent the skin before the deeper vacuum (e.g., before the rate of removal is increased) is applied. The chamber can be positioned about 0.01 mm and about 10 mm from the skin, although larger or smaller distances can be used depending on the application. The chamber can be positioned about 0.01 mm and about 3 mm from the skin. In some embodiments, the chamber is lightly touching the surface of the skin before the deeper vacuum is applied.

In various embodiments, the time duration of treatment vacuum is about 0.1-15 seconds, although larger or smaller values can be used depending on the application.

In various embodiments, the treatment fluence is about 0.1 Joules/cm$^2$-500 Joules/cm$^2$, although larger or smaller fluences can be used depending on the application.

In various embodiments, the treatment pulse duration can be about 1 ns to 30 seconds, although larger or smaller pulse durations can be used depending on the application.

In various embodiments, a treatment beam can be moved between treatment regions at a rate faster than 0.2-2 spots per second, although larger or smaller rates can be used depending on the application.

In various embodiments, the skin can be elevated within about 0.1 sec to 1 sec after applying deeper vacuum.

In various embodiments, the thickness of the index matching layer is about 10 mm-1000 mm, although larger or smaller thickness can be used depending on the application. In some embodiments, the thickness is about 0.01 mm-3 mm.

In various embodiments, the IPL lamp can be a xenon, krypton, or halogen lamp. In various embodiments, the size of the IPL capsule is about 15-40 mm by 15-40 mm by 30-100 mm.

In various embodiments, a mechanism is used to introduce air to break the vacuum seal between the chamber and the skin. In certain embodiments, the flattened skin can become stuck to the surface of the chamber or chamber window. A vacuum release mechanism can facilitate removal of the skin from the chamber surface or chamber window. The mechanism can be located at least 1 meter from the vacuum chamber and pressure inside the chamber can be restored to ambient in less than about 0.5 seconds.

In various embodiments, the mechanism can be a compression pump remote from the located chamber. The compression pump can be about 1-3 meters from the chamber. Tubing connecting the compression pump to the chamber is evacuated during a treatment. With a 3 mm diameter tubing, the additional volume can be more than 5 times the vacuum chamber volume, resulting in a large pump or release time which is longer than 0.5 seconds. This can slow down the total treatment process time, since an application of 1000 pulses over a back can increase the total treatment time by about 500 seconds. By turning on the pressure release 0.3 seconds prior to the termination of the evacuation mode, skin flattening is gradually diminishing; however, the pain blocking effect can still be active. As a result, vacuum release time is effectively reduced without compromising pain blocking. In certain embodiments, the mechanism is capable of capable of vacuum release within a duration smaller than 0.5 sec whereby the vacuum release (e.g., a pump or valve) is located at a distance greater than 1 meter from the skin.

In various embodiments, a system for treating skin can be used for one or more of hair removal, treatment of pigmented lesions, treatment or removal of a tattoo, treatment of fat, treatment of vascular lesions, treatment of acne, skin tightening, skin remodeling, skin rejuvenation, and wrinkle treatments, although other indications can be treated as well.

In various embodiments, the target region can include one or more of an axilla, an underarm, a bikini line, a chin, a region of soft tissue, or a region of fatty tissue. Other target regions can be treated using the technology.

While the invention has been particularly shown and described with reference to specific illustrative embodiments, it should be understood that various changes in form and detail may be made without departing from the spirit and scope of the invention.

What is claimed:

1. A method of treating skin, comprising:
   removing air from inside a chamber positioned adjacent a surface of the skin in a target region prior to forming a substantially fluid tight seal between a rim of the chamber and skin surrounding the target region, impedance of air outside the chamber flowing into the chamber between the rim of the chamber and the skin surface causing the pressure inside the chamber to decrease relative to ambient;
   sensing when the pressure inside the chamber decreases to a threshold value; and
   increasing the rate of removal of the air from inside the chamber upon sensing the threshold value so that (i) the rim of the chamber forms the substantially fluid tight seal with the skin surrounding the target region and (ii) the skin of the target region is drawn toward an inner surface of the chamber.

2. The method of claim 1 further comprising delivering electromagnetic radiation to treat the skin of the target region.

3. The method of claim 1 further comprising drawing the skin into contact with the inner surface of the chamber.

4. The method of claim 1 further comprising using a pressure sensor in fluid communication with the chamber to sense the pressure inside the chamber.

5. The method of claim 1 further comprising positioning the chamber about 0.01 mm to about 3 mm from the surface of the skin before increasing the rate of removal of air.

6. The method of claim 1 further comprising, before increasing the rate of removal of air, positioning the chamber in contact with the surface of the skin without creating a substantially fluid tight seal.

7. The method of claim 1 wherein the removing step comprises modulating the rate of removal of the air from inside the chamber by periodically opening and closing a valve in fluid communication with the chamber.

8. The method of claim 1 wherein the increasing step comprises increasing the rate of removal of the air from inside the chamber by opening a valve in fluid communication with the chamber.

9. The method of claim 1 wherein the chamber is capable of forming the substantially fluid tight seal between the rim of the chamber and soft skin.

10. The method of claim 1 further comprising releasing the substantially fluid tight seal by decreasing the rate of removal of the air from inside the chamber after a predetermined time interval following achieving the threshold value.

11. The method of claim 1 further comprising releasing the substantially fluid tight seal by introducing air into the chamber after a predetermined time interval following achieving the threshold value.

12. The method of claim 1 further comprising disposing a lubricant on a surface of the skin and using the lubricant to facilitate movement of the chamber to a second target region of the skin.

13. The method of claim 1 further comprising providing a treatment for at least one of hair removal, pigmented lesions, tattoo removal, lipid rich tissue, vascular lesions, acne, skin tightening, skin remodeling, and skin rejuvenation.

14. The method of claim 1 further comprising delivering an injection through a surface of the chamber into the skin to provide at least one of a vaccine, collagen, insulin, and botox.

15. The method of claim 2 further comprising disposing an index matching layer on an outer surface of the chamber to facilitate delivery of the electromagnetic radiation.

16. An apparatus for treating skin, comprising:
    a chamber defined by a surface and a rim extending from the surface;
    a first valve in fluid communication with the chamber;
    a second valve in fluid communication with the chamber;
    a source of vacuum in fluid communication with the chamber through the first valve and the second valve, the source of vacuum configured to remove air from inside the chamber through the first valve so that air outside the chamber flows into the chamber, impedance of the air flowing between the rim of the chamber positioned adjacent the skin surface causing the pressure inside the chamber to decrease relative to ambient;
    a pressure sensor in fluid communication with the chamber, the pressure sensor determining when the pressure inside the chamber decreases to a threshold value; and
    a controller in electrical communication with the first valve, the second valve, and the pressure sensor, the controller receiving a signal from the pressure sensor when the threshold value is reached, the controller opening the second valve causing the rate of removal of the air from inside the chamber through the second valve by the source of vacuum to be increased, so that (i) the rim of the chamber forms a substantially fluid tight seal with the skin and (ii) the skin is drawn toward an inner surface of the chamber.

17. The apparatus of claim 16 further comprising an energy source to provide treatment radiation, the energy source in electrical communication with the controller, which triggers the energy source to deliver treatment radiation upon decreasing the pressure inside the chamber to a second threshold value.

18. The apparatus of claim 17 wherein the surface of the chamber is a transparent window, and the treatment radiation is delivered through the transparent window to the target region of skin.

19. The apparatus of claim 17 wherein the surface of the chamber is a translucent window that causes at least a portion of the treatment radiation to be diffused as the treatment radiation is delivered to the target region of skin.

20. The apparatus of claim 16 wherein side walls of the chamber facilitates spacing of the chamber surface from a target region of skin.

21. The apparatus of claim 16 further comprising an injector to provide an injection below the surface of the skin of at least one of a vaccine, collagen, insulin, and botox.

22. An apparatus for treating skin, comprising:
    first means for removing air from inside a chamber positioned adjacent a surface of the skin in a target region so that air outside the chamber flows into the chamber, impedance of the air flowing between a rim of the chamber and the skin surface causing the pressure inside the chamber to decrease relative to ambient;
    means for sensing when the pressure inside the chamber decreases to a threshold value;
    means for controlling the rate of removal of air from inside the chamber upon receiving a signal from the means for sensing that pressure inside the chamber decreased to the threshold value; and
    second means for removing air from inside the chamber, the means for controlling opening the second means for removing air upon receiving the signal from the means for sensing such that the rate of removal of the air from inside the chamber increases and (i) the rim of the chamber forms a substantially fluid tight seal with the skin and (ii) the skin is drawn toward an inner surface of the chamber.

23. The method of claim 7 wherein the increasing step further comprises increasing the rate of removal of the air from inside the chamber by opening a second valve in fluid communication with the chamber.

24. The apparatus of claim 16 wherein the first valve is adapted to periodically open and close before the threshold value is reached to modulate the rate of removal of air inside the chamber.

* * * * *